United States Patent [19]

Banholzer

[11] Patent Number: 5,952,505
[45] Date of Patent: Sep. 14, 1999

[54] PROCESS FOR PREPARING PURE ENANTIOMERS OF TROPIC ACID ESTERS

[75] Inventor: Rolf Banholzer, Stuttgart, Germany

[73] Assignee: Boehringer Ingelheim KG, Ingelheim, Germany

[21] Appl. No.: 08/945,142

[22] PCT Filed: Apr. 26, 1996

[86] PCT No.: PCT/EP96/01779

§ 371 Date: Nov. 19, 1997

§ 102(e) Date: Nov. 19, 1997

[87] PCT Pub. No.: WO96/33996

PCT Pub. Date: Oct. 31, 1996

[30] Foreign Application Priority Data

Apr. 28, 1995 [DE] Germany .......................... 195 15 625

[51] Int. Cl.⁶ ....................... C07D 451/06; C07D 451/14
[52] U.S. Cl. ........................................... 546/127; 546/112
[58] Field of Search ..................................... 546/127, 112

[56] References Cited

FOREIGN PATENT DOCUMENTS 1.289.429  2/1962  France .

OTHER PUBLICATIONS

Synthesis, 1976, Stuttgart, DE, Seiten 311–312, XP002011575 V.A. Fung et al.: "A convenient systhesis of N–CD3 Labelled Tropine and Atropine"—siehe Seite 312.

"General Synthesis of Tropane Alkaloids via the Polybromo Ketone–Iron Carbonyl Reaction", Y. Hyakawa et al., *J.Am. Chem. Soc.* 100 (1978) 1786–1790.

*Primary Examiner*—Alan L. Rotman
*Attorney, Agent, or Firm*—R. P. Raymond; M-E. M. Devlin; A. R. Stempel

[57] ABSTRACT

Precursors of anticholinergically active quaternary compounds can be synthesized from optically active tropic acid by acetylation, conversion into the acid chloride, reaction with amino alcohols of formula (I)

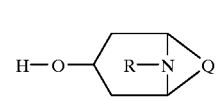

(as the methanesulphonate; Q and R are explained in the specification), deacetylation and isolation of the reaction product.

4 Claims, No Drawings

PROCESS FOR PREPARING PURE ENANTIOMERS OF TROPIC ACID ESTERS

The invention relates to a process by which esters of (+)- and (−)-tropic acid can be prepared with a high degree of purity and in good yields.

The problem of synthetically producing enantiomerically pure esters of (+)- and (−)-tropic acid has not hitherto been solved with any degree of satisfaction. The enantiomeric separation of racemic tropic acid esters also frequently comes up against surprising experimental problems and cannot generally be carried out. This applies particularly to the higher substituted homologues and analogues of atropine, such as N-isopropylnoratropine, the precursor of the commercial product ipratropium bromide.

The conventional synthesis of tropic acid esters according to I. Mamlock and R. Wolffenstein (Ber. dtsch. Chem. Ges. 41, 731 (1908)), in which O-acetyltropic acid chloride is reacted with tropine hydrochloride does not produce satisfactory results, possibly on account of the poor solubility of tropine hydrochloride. The method has not been used for optically active tropic acid.

The process is problematic because side reactions can easily occur. This is true of basic conditions, with which there is a danger that water is eliminated, whilst on the other hand the use of salts of the amino alcohols, which are usually poorly soluble, requires elevated temperatures which can lead to the formation of highly disruptive by-products; mention should be made particularly of dehydrated compounds (apocompounds) and dimerization products.

It has now been found that substantially enantiomerically pure (+)- and (−)-tropic acid esters of amino alcohols of the formula

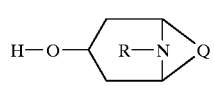

(I)

wherein

Q denotes $CH_2$—$CH_2$, $CH_2$—$CH_2$—$CH_2$, CH=CH or

R denotes a straight-chained or branched $C_{1-4}$-alkyl group, can surprisingly be prepared by (a) acetylating the corresponding optically active tropic acid,
(b) converting the resulting O-acetyl tropic acid with thionyl chloride into the acid chloride,
(c) reacting the latter at ambient temperature in an inert solvent, optionally with the addition of excess aluminum oxide, with the methanesulphonate of an amino alcohol of formula I,
(d) deacetylating the resulting compound by the action of a strong acid and
(e) isolating the optically active tropic acid ester obtained.

The (+)- and (−)-tropic acid required as starting material can be obtained from D,L-tropic acid by first preparing a salt with an optically active base in a manner known per se and recrystallising this salt several times. A suitable base might be, for example, (−)-quinine whilst the solvent for crystallization might be ethanol. The (+)-tropic acid thus prepared has a purity of 99.8% ($[\alpha]_D^{20}$=+73.1; c=1 in ethanol).

The reaction according to (a) is preferably carried out at ambient temperature and the reaction according to (b), which is carried out immediately afterwards, is preferably performed at ambient temperature or slightly elevated temperature without intermediate isolation of the acetylated acid.

Step (c) takes place within a few days, when the methanesulphonate of a compound of formula (I) is reacted in an inert solvent, such as methylene chloride, at temperatures between 0° C. and about 30° C., preferably at ambient temperature, with stirring, whilst excess aluminium oxide may be used to bind the acid. Once the solvent has been eliminated under reduced pressure, the residue can be further processed directly.

In step (d), favourable results are obtained if the deacetylation is carried out with a dilute aqueous inorganic acid, such as 2–20% hydrochloric acid, preferably 3–10% hydrochloric acid, at ambient temperature. Thus, for example, total reaction is obtained with 5% hydrochloric acid within about 2 days.

The reaction product can be isolated as a base (step (e)) by stirring the acidic reaction solution into excess dilute (e.g. 20%) sodium hydroxide solution or into aqueous alkali metal carbonate solution and filtering off the crystalline product precipitated. Temperatures of between −15 and +50° C. may be used; it is preferable to use sodium carbonate solution at about 20° C. The salts, e.g. the corresponding hydrochloride, can easily be prepared from the base by adding a stoichometric quantity of ethereal hydrochloric acid to the solution of the base, e.g. in methylene chloride.

The esters obtained in this way consist of more than 99% of the pure optically active compound, assuming that the starting acid is correspondingly pure.

The optically active esters which may be obtained according to the invention are valuable intermediate products for producing the corresponding anticholinergic quaternary compounds, such as the corresponding methobromides or methomethanesulphonates, which may be used, for example, as agents for treating asthmatic diseases or obstructive diseases of the respiratory tract.

The quaternary compounds may be prepared by conventional methods without racemisation.

The reaction according to the invention is explained more fully in the Examples which follow, but the reaction conditions according to the invention are not limited to the specific data provided.

EXAMPLE 1

(−)-Tropic acid-N-isopropylnortropine ester hydrochloride (a) 13.3 g of (−)-Tropic acid are added to 31.4 g of acetyl chloride with stirring at ambient temperature and within one hour a clear solution is formed. After another hour, the reaction is virtually complete, according to thin layer chromatography (TLC). 47.5 g of thionyl chloride are added dropwise to the (−)-O-acetyl tropic acid solution over 30 minutes. The solution is stirred overnight at ambient temperature, then for a further hour at 50° C. After evaporation at 35° C. under reduced pressure, 18.9 g of a brownish liquid remain, $[\alpha]_D^{20}$=−87.8 (c=0.5 in chloroform). The presence of the desired compound can be confirmed by spectroscopy.

(b) 7.26 g (0.0275 mol) of N-isopropylnortropine methanesulphonate and 6.20 g (0.0275 mol) of the product obtained in (a) are stirred in 45 ml of methylene chloride at ambient temperature. After seven days the reaction solution is evaporated down under reduced pressure at 30° C. The residue (16.9 g) is used for the next step without being further worked up.

(c) 11.1 g of the product according to (b) are dissolved in 60 ml of 5% hydrochloric acid and stirred for 2 days at ambient temperature. TLC indicates quantitative deacetylation.

The reaction solution is extracted twice with a little diethylether, then any residual ether is eliminated under reduced pressure. Excess 20% aqueous sodium carbonate solution is then stirred into the solution, and a crystalline product is precipitated. It is filtered off and washed with cold water until the filtrate running away shows only a slightly alkaline reaction, and is then dissolved in methylene chloride.

After drying over sodium sulphate, the solvent is distilled off under reduced pressure and the residue is recrystallised from acetonitrile. White crystals are obtained, m.p. 131° C., $[\alpha]_D^{20}=-19.1$ (c=1 in ethanol). In order to prepare the hydrochloride, the solution of the base in methylene chloride is combined with the stoichiometric amount of ethereal hydrochloric acid. After the product has been recrystallised from ethanol and acetonitrile, the (−)-tropic acid-N-isopropylnortropine ester hydrochloride is obtained in the form of white crystals, m.p. 214–8° C.

$[a]_D^{20}=-27.8$ (c=1 in water); optical purity >99.8%.

The presence of the compound was confirmed by elemental analysis and spectroscopy.

Quaternization to obtain the methobromide is carried out, for example, by reacting with methyl bromide in methylene chloride/acetonitrile at ambient temperature. White crystals are obtained (yield 75.2% of theory, m.p. 238–42° C. with decomposition).

$[\alpha]_D^{20}=-24.5$ (c=1 in water); optical purity >99.5%.

The presence of the compound was confirmed by elemental analysis and spectroscopy.

EXAMPLE 2

(+)-Tropic acid-N-isopropylnortropine ester-hydrochloride

Starting from (+)-tropic acid, which may be obtained by racemate cleaving from D,L-tropic acid with (−)-quinine, $[\alpha]_D^{20}=+73.1$ (c=1 in ethanol; optical purity 99.8%), the title compound is obtained analogously to Example 1 in the form of white crystals, m.p. 214–7° C., with decomposition, $[\alpha]_D^{20}=+27.8$ (c=1 in water). Yield 55.7% of theory. Once again, the presence of the compound is confirmed by elemental analysis and spectroscopy.

As described in Example 1, the compound obtained is reacted to form the methobromide; m.p. 238–41° C. (decomp.), $[\alpha]_D^{20}=+25.3$ (c=1 in water).

For reacting the O-acetyltropic acid chlorides with the compounds (I), yields of between 60 and 70% are obtained if the reactions continue at room temperature for several days, and in addition to methylene chloride, for example, dimethylformamide or acetonitrile as reaction medium will give similar results.

I claim:

1. A process for preparing enantiomerically pure (+)-tropic acid esters of an amino alcohol of Formula (I)

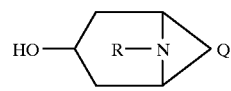

Formula (I)

wherein Q is $CH_2-CH_2$, $CH_2-CH_2-CH_2$,

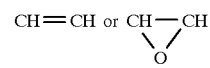

and

R is a straight-chained or branched $C_{1-4}$-alkyl group which comprises the steps of (a) acetylating a tropic acid of Formula A

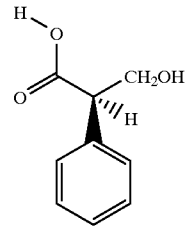

Formula A with acetychloride to form acetylated tropic acid of Formula (B)

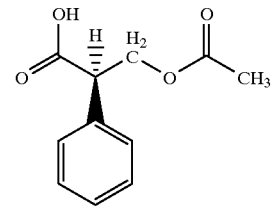

Formula (B)

(b) converting for acetylated tropic acid (B) into acetylated tropic acid chloride of Formula (C).

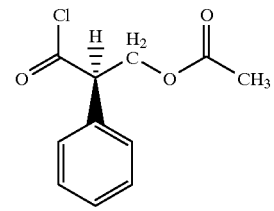

Formula (C)

with thionyl chloride;

(c) reacting the acetylated tropic acid chloride (C) at ambient temperature in an inert solvent with the methanesulphonate of the amino alcohol of Formula (I) in the presence of an excess of aluminum oxide to form a tropic acid ester of Formula (D)

Formula (D)

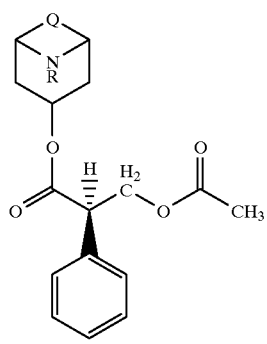

(d) deacetylating the tropic acid ester (D) in the presence of about 2 to about 20% hydrochloric acid to form deacetylated tropic acid ester of Formula (E)

Formula (E)

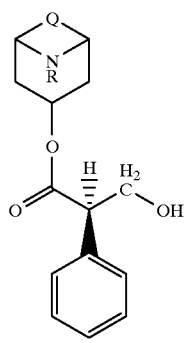

(e) isolating the deacetylated tropic acid ester (E) as a free base by treating with an excess of an aqueous sodium hydroxide or an alkali carbonate solution at a temperature of about −15° C. to about 50° C.

2. The process recited in claim 1 wherein N-isopropylnortropine is the amino alcohol of Formula (I).

3. A process for preparing enantiomerically pure (−)-tropic acid esters of an amino alcohol of Formula (I)

Formula (I)

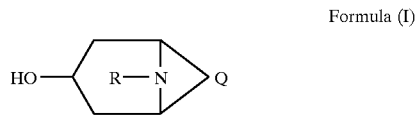

wherein Q is $CH_2$—$CH_2$, $CH_2$—$CH_2$—$CH_2$,

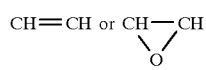

and

R is a straight-chained or branched $C_{1-4}$-alkyl group which comprises the steps of (a) acetylating a tropic acid of Formula (A')

Formula (A')

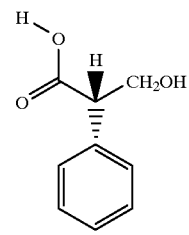

with acetychloride to form an acetylated tropic acid of Formula (B')

Formula (B')

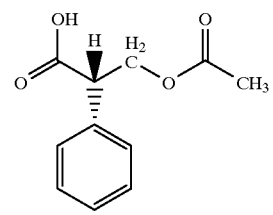

(b) converting the acetylated tropic acid (B) into acetylated tropic acid chloride of Formula (C')

Formula (C')

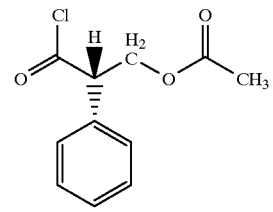

with thionyl chloride;

(c) reacting the acetylated tropic acid chloride (c) at ambient temperature in an inert solvent with the methanesulphonate of the amino alcohol of Formula (I) in the presence of an excess of aluminum oxide to form a tropic acid ester of Formula (D')

Formula (D')

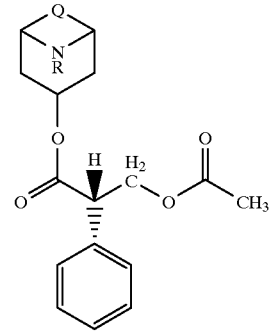

(d) deacetylating the tropic acid ester (D') in the presence of about 2 to about 20% hydrochloric acid to form deacetylated tropic acid ester of Formula (E')

Formula (E')
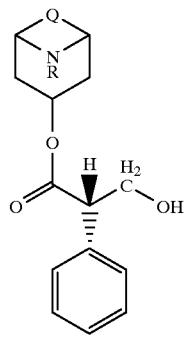
(e) isolating the deacetylated tropic acid ester (E') as a free base by treating with an excess of an aqueous sodium hydroxide or an alkali carbonate solution at a temperature of about −15° C. to about 50° C.
4. The process as recited in claim 3 wherein N-isopropylnotropine is the amino alcohol of Formula (I).
* * * * *